United States Patent [19]

McLachlan et al.

[11] Patent Number: 4,829,186

[45] Date of Patent: May 9, 1989

[54] METHODS AND APPARATUS FOR MEASURING THE LIGHT ABSORBANCE OF A FLUID MEDIUM

[75] Inventors: Richard D. McLachlan; Ray W. Chrisman; Mary Anne Lengers, all of Midland, Mich.

[73] Assignee: The Dow Chemical Company, Midland, Mich.

[21] Appl. No.: 214,902

[22] Filed: Jun. 28, 1988

Related U.S. Application Data

[63] Continuation of Ser. No. 748,657, Jun. 25, 1985, abandoned.

[51] Int. Cl.$^4$ .............................................. G01N 21/33
[52] U.S. Cl. ..................................... 250/373; 356/51
[58] Field of Search ................. 356/51, 300, 128, 135, 356/136; 250/373

[56] References Cited

U.S. PATENT DOCUMENTS

| | | | |
|---|---|---|---|
| 3,733,130 | 5/1973 | Young | 250/227 |
| 3,751,672 | 8/1973 | Michel et al. | 356/136 |
| 3,917,410 | 11/1975 | Ulrich | 356/128 |
| 4,228,192 | 10/1980 | Sanden | 250/340 |
| 4,427,293 | 1/1984 | Harmer | 356/136 |
| 4,602,869 | 7/1986 | Harrick | 356/440 |

OTHER PUBLICATIONS

"Infrared ATR Determination of Alcohols in Aqueous Solution", Malone et al., *Spectrochemic or Acta* 8/1965, pp. 1361–1366.

"Application of Attenuated Total Reflectance IR Spectroscopy to Toilet Articles and Household Products 2-Quantative Analysis", Puttnam et al., J. Soc. Cosmetic Chemist, 1/1966, pp. 9–16, vol. 17.

*Primary Examiner*—F. L. Evans
*Attorney, Agent, or Firm*—John K. McCulloch

[57] ABSTRACT

The presence and concentration of a light absorbing constituent in a fluid medium is determined in-situ by immersing in such medium a probe having a prism at one end whose refractive index is greater than that of the medium and causing light including a wavelength absorbable by such constituent to traverse an optical path through the prism and undergo successive attenuated total reflections. At each reflection some of the light will be absorbed by the constituent. The intensity of light emerging from the prism is measured at one or more wavelengths, including one absorbable by such constituent. The concentration of the constituent is determined by comparison of the measured intensity with values obtained from like measurements performed on like mediums containing known concentrations of the constituent.

21 Claims, 2 Drawing Sheets

METHODS AND APPARATUS FOR MEASURING THE LIGHT ABSORBANCE OF A FLUID MEDIUM

This is a continuation of co-pending application Ser. No. 748,657 filed on June 25, 1985, now abandoned.

This invention relates to the measurement of concentrations of light absorbing constituents of fluid mediums. It is particularly useful for in-situ analyses of mediums having high absorbance characteristics.

BACKGROUND OF THE INVENTION

Absorption spectroscopy in the ultraviolet (UV) wavelength range is a widely used method for analysis of organic materials which absorb UV radiation. Due to the high absorptivities (i.e., large extinction coefficients) of UV absorbing compounds, absorption measurements customarily are performed on samples diluted with UV transparent solvents. Dilution factors of 100 to 10,000 commonly are employed in conjunction with absorption cells having pathlengths of 1 mm to 10 cm. Absorption measurements of undiluted samples would require the use of cells with pathlengths on the order of 1 micrometer. The necessity of either diluting the sample or employing absorption cells of inconveniently short pathlengths has severely limited the application of UV absorption spectroscopy for in-situ analyses in chemical processes.

SUMMARY OF THE INVENTION

The concentrations of light absorbing constituents of a fluid medium are determined by the use of a fiber optic probe having two groups of optical fibers optically coupled to a transparent light refracting member such as a prism whose refractive index exceeds that of the medium to be analyzed. One group of fibers is used to transmit to a prism light including a wavelength that can be absorbed by a particular constituent of the medium. The prism has at least two angularly displaced, adjacent faces in contact with the medium. Within the prism the light undergoes successive attenuated total internal reflections and emerges from the prism via the second group of optical fibers which transmit the reflected light outwardly of the probe to apparatus which measures the intensities of the reflected light at one or more wavelengths. The measured values of the intensities thus obtained are compared with corresponding values obtained in the same way using like mediums, but containing known concentrations of the constituent, thereby enabling the concentration of the absorbing constituent in the medium under analysis to be determined.

THE DRAWINGS

DETAILED DESCRIPTION

Figure 1:
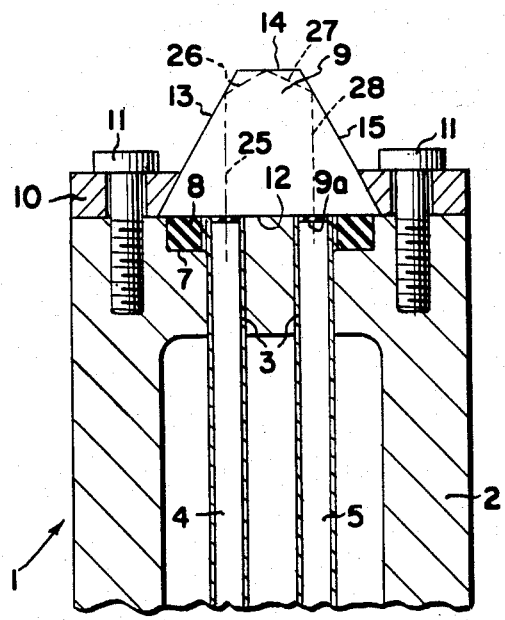
FIG. 1 is a fragmentary, vertical sectional view taken on the line 1—1 of FIG. 2 and illustrating a probe according to one embodiment of the invention.

The invention is predicated on the concept that, when light traveling within a medium impinges upon a boundary between that medium and a medium of lower refractive index, it either passes into the second medium or is totally internally reflected, depending on whether the quantity $n/n'$ sin I (where n and n' are the refractive indices of the first and second mediums, respectively, and I is the angle of incidence) is less than or greater than one. If $n/n'$ sin I is greater than one, total internal reflection occurs. Although the internal reflection is referred to as total, the light, during the reflection process, penetrates a short distance into the second medium. The depth of penetration depends in a complex, known manner on the refractive indices of the two mediums and the angle of incidence, but usually is on the order of tenths of the wavelength of the light. If the incident light includes a wavelength absorbed by a constituent of the second medium, light of such wavelength will be partially absorbed or attenuated during reflection due to the penetration of the light into the second medium. This effect is called attenuated total reflection (ATR). Due to the very shallow penetration of the light into the second medium, ATR is a useful technique for measuring absorbance by strongly absorbing materials.

The requirement that the refractive index of the prism exceed that of the medium limits the choice of prism materials. For use in the mid-ultraviolet region (200–300 nm wavelengths), only silica ($n=1.51$ at 250 nm), sapphire ($n=1.84$ at 250 nm), and diamond ($n=2.7$ at 250 nm) have sufficiently high refractive indices and transmissions to be useful. Silica is useful only for samples of relatively low refractive index, such as aqueous solutions. Diamond is very expensive and does not transmit wavelengths below 225 nm. Thus, sapphire is the most useful material for ATR measurements in the UV range.

In-situ ATR measurements conveniently can be made according to the invention by the use of a probe having a hollow housing formed of material that can be immersed in a fluid medium containing a constituent capable of absorbing light of a specific wavelength. Light of preferably substantially constant intensity is conducted from a source remote from the medium via one or more optical fibers to one end of the probe. At the other end of the probe is a prism having a plurality of angularly displaced, adjacent faces in contact with the medium. Light transmitted to the probe is totally internally reflected from the first face of the prism to each other face thereof in succession and from the last face to one or more optical fibers which conduct the reflected light out of the probe to apparatus for measuring its intensity. Each time the light is reflected within the prism, the absorbing constituent in the medium will absorb some of the light, thereby reducing its intensity. The intensity of light transmitted by the probe at wavelengths absorbed by a constituent thus is inversely related to the concentration of that constituent.

The apparatus may be calibrated by immersing the probe in two or more calibrating mediums and measuring in each case the intensity of the transmitted light at a wavelength absorbed by a particular constituent in each medium. The calibrating mediums correspond to that to be analyzed, but contain known concentrations of the light absorbing constituent. The apparatus then may be used in a like manner to measure the intensity of transmitted light following immersion of the probe in a like medium containing a like constituent of unknown concentration. The intensities obtained from the calibrating mediums and the medium under analysis may be compared to obtain the concentration of the absorbing constituent in the latter medium.

The effective path of the light in a medium being analyzed is approximately proportional to N/cos I, where N is the number of reflections and I is the angle of incidence. The upper limit of the refractive index (n') of the fluid medium is given by the formula $n' = n \sin I$, where n is the refractive index of the prism material. Since the choice of the prism materials is limited, it is convenient to vary the angle of incidence and/or the number of reflections to accommodate samples of various refractive indices and absorbtivities.

A probe 1 according to the embodiment of FIG. 1 has a hollow body 2 formed of metal or other material suitable for immersion in a chemical process fluid that is to be analyzed. Each end of the body is closed except for openings 3 which accommodate known clad optical fibers. In this embodiment there are three fibers 4, 5, and 6, respectively, fixed in the openings 3, but there can be as few as two such fibers diametrally opposite one another. At one end of the body is an external groove 7 which accommodates a sealing ring 8 that encircles the openings 3. Seated on the sealing ring is a light refracting member which may comprise a trapezoidal prism 9 formed of high refractive index material, such as sapphire. Between the prism and the confronting ends of the optical fibers is an optical coupling gel or oil 9a. A clamp 10 maintains the prism in place at the end of the probe and is secured to the body by screws 11. The prism has a flat base 12 and three external faces 13, 14, and 15.

Figures 7, 8:
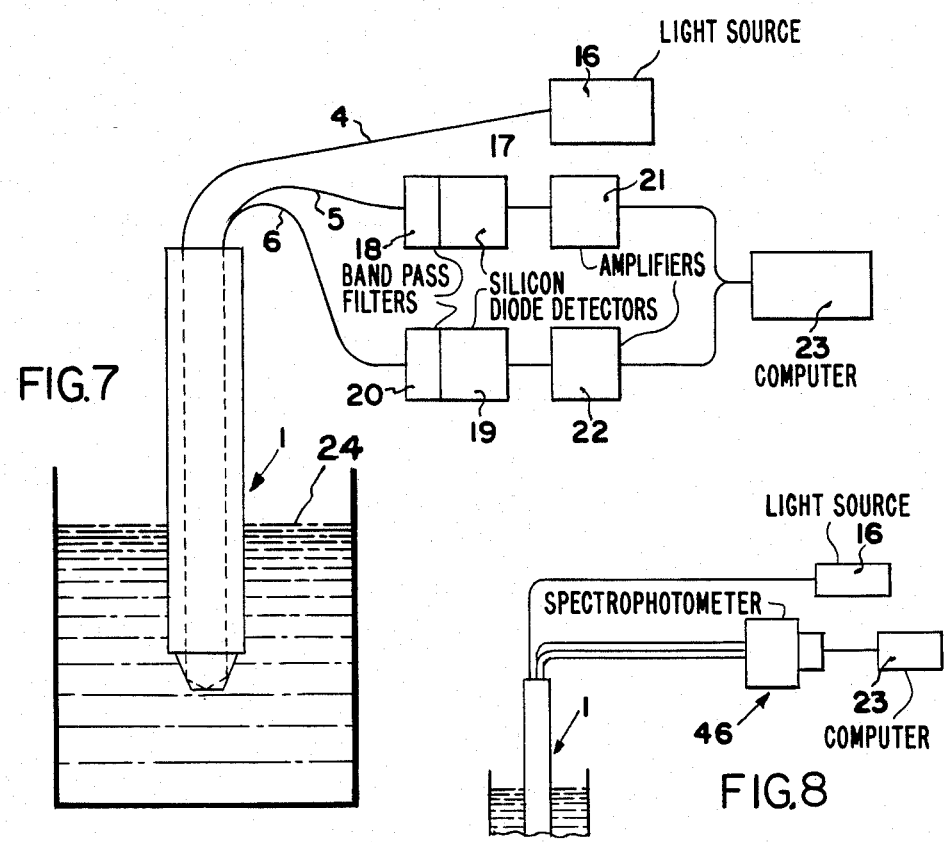
FIG. 7 is a diagrammatic view illustrating apparatus required for performing the process according to one embodiment.
FIG. 8 is a view similar to FIG. 7, but illustrating a modified embodiment of the apparatus.

To condition the apparatus thus far described for use, one of the optical fibers that extends from the probe body 2 is coupled to a substantially constant intensity light source 16 that is remote from the probe. The light source may be a deuterium lamp if light in the UV range is to be used. As shown in FIG. 7 the fiber 4 is coupled to the light source and such fiber hereinafter will be referred to as the input fiber. The other two fibers 5 and 6 shown in FIGS. 2 and 7 will be referred to hereinafter as output fibers.

The output fiber 5 is optically coupled to a silicon diode detector 17 via a bandpass filter 18 and the output fiber 6 also is coupled to a similar detector 19 via a bandpass filter 20. The filters isolate two discrete, different wavelengths. The outputs from the detectors 17 and 19 are amplified by transimpedance amplifiers 21 and 22, respectively, and transmitted to a computer 23 which measures the intensities of the respective wavelengths and computes the concentration of the associated constituent.

Figure 2:
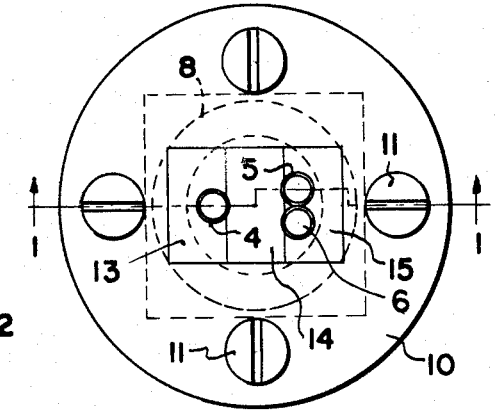
FIG. 2 is a top plan view of the probe shown in FIG. 1.

In the embodiment shown in FIGS. 1, 2, and 7, that end of the probe 1 from which the prism 9 projects is immersed in a fluid medium 24 containing a constituent that will absorb light of a particular wavelength. The light emitted by the source 16, includes the particular wavelength absorbable by the constituent and is conducted by the input fiber 4 to the base 12 of the prism 9 along a path that is normal to the base. Light enters the prism and is transmitted along a path 25 which impinges on the side 13 at an angle of incidence which effects total internal reflection of the light along a path 26 to the side 14 where total internal reflection again occurs to cause the light to travel along a path 27 to the side 15 where once again the light is totally reflected along a path 28 toward the prism base 12. Light emitted from the input fiber diverges as it traverses the optical path through the prism. The overall length of such optical path is so selected as to illuminate both of the output fibers 5 and 6 from the single input fiber.

Assuming that the filter 18 transmits light of a wavelength not absorbed by any constituent of the medium, then the signal from the detector 17 constitutes a calibration signal. If the filter 20 transmits light of a frequency absorbed by the constituent, then the signal from the detector 19 will vary inversely with the concentration of the absorbing constituent. The ratio of the respective signals, as determined by the computer, enables the concentration of the absorbing constituent to be determined.

It is not necessary that two output fibers be used; one is sufficient. However, the use of two output fibers enables the calibration and the concentration procedures to be conducted simultaneously, whereas if a single output fiber were used the calibration would require the immersion of the probe in a medium corresponding to the medium 24, but from which the absorbing constituent has been omitted. In this instance the values of the calibrating and the other intensities have to be determined sequentially and then compared.

For the process according to the invention to function reliably, it is necessary that each output fiber be illuminated fully. It is desirable to minimize the length of the optical path in the prism because of the divergence of the transmitted light and the consequent reduction of its intensity.

Figure 4:
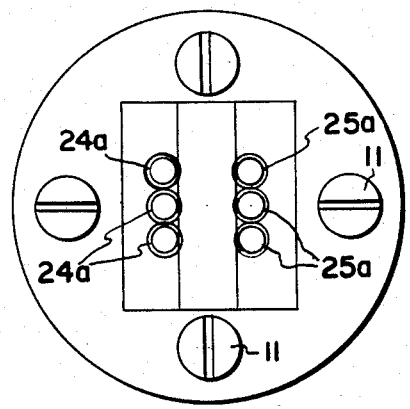
FIG. 4 is a view similar to FIG. 2, but illustrating a further embodiment.

It is not necessary that the probe be limited to a single input fiber or to one or two output fibers. FIG. 4 illustrates a probe having three input fibers 24a and three output fibers 25a. Light emitted from each of the input fibers will illuminate more than one of the output fibers. Thus, a construction having three input fibers and three output fibers may transmit as much as four to eight times as much light as a two-fiber probe and enable the analysis of the concentrations of multiple constituents simultaneously.

Figure 3:
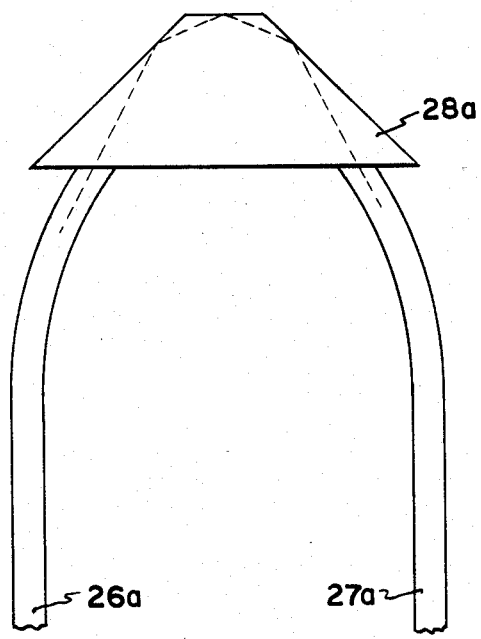
FIG. 3 is a diagrammatic view similar to FIG. 1, but illustrating a second embodiment.

FIG. 3 illustrates an embodiment of the invention which differs from the others in that the input and output optical fibers 26a and 27a are inclined with respect to the probe axis by an angle of 10° to 30° and converge in a direction toward a prism 28a. The base angles are reduced appropriately. This results in an increase in the angle of incidence and thus allows the probe to operate in mediums of higher refractive index.

If the refractive index of the prism shown in FIG. 3 is different from that of the optical fibers, light will be refracted on entering and leaving the prism. The angle x' between the axis of the optical path entering the prism and the probe axis is related to the angle x between the fiber axis and the probe axis by the relation $\sin x' = n^*/n \sin x$, where $n^*$ is the refractive index of the fiber and n is the refractive index of the prism. The angle of incidence is given by $$I = \frac{180 + x'}{3} = \frac{180 + \sin^{-1}\left[\frac{n^*}{n} \sin x\right]}{3}.$$

A probe according to FIG. 3 may include a sapphire prism and quartz fibers with an angle of 30° between the fiber axes and the probe axis. Such a probe has an angle of incidence of about 68°. It is thus useful in analyzing materials having refractive indices as high as 1.71 at 250 nm.

Figures 5, 6:
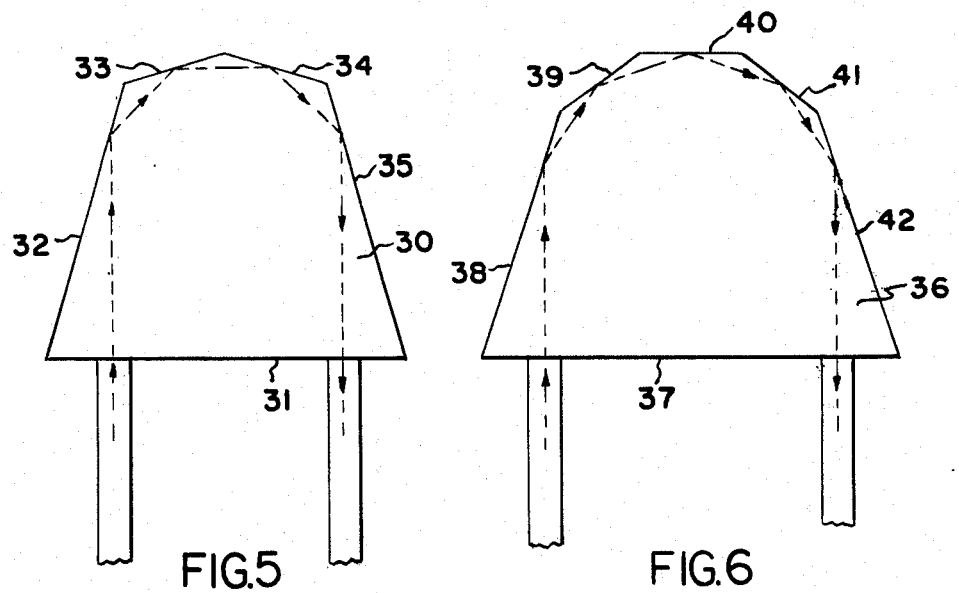
FIGS. 5 and 6 are diagrammatic views illustrating other forms of prisms which may be used with the probes.

The number of reflections to which the transmitted light is subjected is not limited to two or three. FIG. 5 shows a prism 30 having a base 31 and four faces 32, 33, 34, and 35 which produce four reflections. The angles of incidence and the base angles are 67.5°. The prism 36 of FIG. 6 has a base 37 and five faces 38, 39, 40, 41, and 42 which produce five reflections. The angles of incidence and the base angles are 72°.

Probes producing four and five reflections also can be constructed with fibers that are parallel to the probe axis. Such a probe having five reflecting surfaces, and its fiber axes inclined 30° with respect to the probe axis, has angles of incidence of about 77°. Thus it is useful in samples with refractive indices up to about 1.79 at 250 nm.

Probes with larger angles of incidence and larger numbers of reflecting surfaces could be constructed, but these would not increase significantly the range of refractive indices inasmuch as the ultimate limit is 1.84, i.e., the refractive index of the sapphire prism material.

For many applications, it is desirable to maximize the light transmissions through the prism. For maximum light transmission the optical fibers should have relatively large core diameters. Fibers with core diameters of about 0.6 mm are preferred because larger fibers are more expensive and difficult to handle due to their large bending radii. It is desirable to minimize the length of the optical path in the prism because of the divergence of the transmitted light and the consequent reduction in its intensity.

The light transmission can be increased by the use of multiple fibers to conduct light to and from the prism. Within limits imposed by the size and aperture angle of the light source, the amount of light conducted to the prism is proportional to the total surface area of the fiber ends, i.e., to the product of the cross sectional area of one fiber and the number of input fibers. Standard deuterium lamps with apertures of 1 mm can fully illuminate three fibers with core diameters of 0.6 mm and a numerical aperture of 0.25.

A probe according to FIG. 4 could have its output fibers 25 coupled to three filter-detector systems of the kind shown in FIG. 7 for measuring the transmittance at three different wavelengths, thus allowing simultaneous measurements of the concentrations of two components. Alternatively, the output fibers of any of the probes can be arranged linearly as shown in FIG. 8 and coupled to a spectrophotometer 46 for scanning a spectrum. Systems can be constructed to allow analyses of samples with three or more components.

What is claimed is:

1. In a method of determining the concentration of at least one light absorbing constituent in a fluid medium composed of a plurality of different constituents, said method including:
   (a) immersing in said medium a probe at one end of which is light refractive means having a refractive index greater than that of said medium and an outer surface in contact with said medium; and
   (b) transmitting to said refractive means via said probe from a source remote from the latter light of substantially constant intensity having at least one wavelength absorbable by said one constituent and at such angle of incidence as to be totally internally reflected a number of times within said refractive means to cause said reflected light to emerge from said probe;
   the improvement comprising:
   (c) selecting said light from the ultraviolet range of wavelengths;
   (d) limiting the number of internal reflections within said refractive means to not more than five; and
   (e) measuring the intensity of the light of said one wavelength following its emergence from said probe.

2. The method according to claim 1 wherein said refractive means comprises a prism.

3. The method according to claim 1 wherein the light transmitted to said refractive means enters and leaves the latter in opposite directions along spaced, substantially parallel paths.

4. The method according to claim 1 wherein the light transmitted to said refractive means and the light reflected from said refractive means enter and leave said refractive means in opposite directions along spaced paths that converge in a direction toward said refractive means.

5. In a method of determining the concentration of at least one light absorbing constituent in a fluid medium composed of a plurality of different constituents, said method including:
   (a) immersing in said medium a probe at one end of which is light reflective means having a refractive index greater than that of said medium and an outer surface in contact with said medium; and
   (b) transmitting to said refractive means via said probe from a source remote form the latter light of substantially constant intensity having at least one wavelength absorbable by said one constituent and at least one other wavelength not absorbable by said one constituent and at such an angle of incidence as to be totally internally reflected a number of times within said refractive means and emerge from said probe;
   the improvement comprising:
   (c) selecting said one wavelength from the ultra violet range of wavelengths;
   (d) limiting the number of internal reflections of said light to not more than five; and
   (e) measuring the intensity of the reflected light of each of said wavelengths to obtain a ratio therebetween.

6. The method according to claim 5 wherein the light transmitted to said refractive means includes a frequency absorbable by each of said constituents.

7. In a probe for determining the concentration of at least one light absorbing constituent in a fluid medium composed of a plurality of different constituents, said probe including:
   (a) a fluid tight housing immersible in said medium and terminating at one end in light refractive means having a refractive index greater than that of said medium and an outer surface exposed for contact with said medium;

(b) at least one optical input fiber for transmitting through said housing to said refractive means light of substantially constant intensity having a wavelength absorbable by said one constituent and at such angle of incidence that said light is totally internally reflected repeatedly within said refractive means and thence outwardly thereof;

(c) and at least one optical output fiber alongside said input fiber for collecting light reflected outwardly of said refractive means;

the improvement wherein:

(d) said wavelength is in the ultra violet range of wavelengths; and (e) the number of said internal reflections is not more than five.

8. A probe according to claim 7 including a plurality of said output fibers.

9. A probe according to claim 7 including a plurality of said input fibers and a plurality of said output fibers.

10. A probe according to claim 7 wherein said refractive means comprises a prism having at least three angularly displaced faces.

11. A probe according to claim 10 wherein said prism has four of said faces.

12. A probe according to claim 10 wherein said prism has five of said faces.

13. A probe according to claim 7 wherein said input and output fibers have parallel ends confronting said refractive means.

14. A probe according to claim 7 wherein said input and output fibers have corresponding ends arranged on lines which converge in the direction of said refractive means.

15. In apparatus for determining, in a fluid medium composed of a plurality of different constituents, the presence of at least one light absorbing constituent, said apparatus including:

(a) a probe having a housing formed of material suitable for immersion in said medium without adverse effect;

(b) transparent light refractive means at one end of said housing having a refractive index greater than that of said medium; and (c) a source of light of substantially constant intensity including a wavelength absorbable by said one constituent;

the improvement comprising:

(d) an optical input fiber supported by said probe for transmitting light from said source and in one direction through said housing to said refractive means at such angle of incidence as to be totally internally reflected up to five times within said refractive means and thence outwardly thereof;

(e) an optical output fiber supported by said probe alongside said input fiber for collecting light reflected outwardly of said refractive means and transmitting such light in the opposite direction through said housing; and (f) means coupled to said output fiber for measuring the intensity of light transmitted thereby, (g) said wavelength being selected from the ultra violet range of wavelengths.

16. Apparatus according to claim 15 wherein said light source emits light of at least two different wavelengths one of which is not absorbable by said one constituent, and wherein said apparatus includes a second optical output fiber adjacent said one output fiber, and second light intensity measuring means coupled to said second output fiber for measuring the intensity of light transmitted thereby.

17. Apparatus according to claim 15 including a plurality of said output fibers, and a corresponding plurality of said light intensity measuring means coupled to the respective output fibers.

18. Apparatus according to claim 15 wherein said refractive mans comprises a prism having more than two plane, adjacent, angularly displaced faces.

19. Apparatus according to claim 18 wherein said prism has three of said faces.

20. Apparatus according to claim 18 wherein said prism has four of said faces.

21. Apparatus according to claim 18 wherein said prism has five of said faces.

* * * * *

UNITED STATES PATENT AND TRADEMARK OFFICE
Certificate

Patent No. 4,829,186                                              Patented: May 9, 1989

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is Richard D. McLachlan, Midland, Mich., Ray W. Chrisman, Midland, Mich. and MaryAnne Leugers, Midland, Mich.

Signed and Sealed this Twenty-fifth Day of July, 1989

*Abraham Hershkovitz*
*Petitions Examiner*
*Office of the Deputy Assistant*
*Commissioner for Patents*

UNITED STATES PATENT AND TRADEMARK OFFICE
CERTIFICATE OF CORRECTION

PATENT NO. : 4,829,186

DATED : May 9, 1989

INVENTOR(S) : Richard D. McLachlan et al

It is certified that error appears in the above-identified patent and that said Letters Patent is hereby corrected as shown below:

Column 6, line 36, change "reflective" to -- refractive --.

Column 8, line 36, change "mans" to -- means --.

Signed and Sealed this

Twenty-first Day of November, 1989

Attest:

JEFFREY M. SAMUELS

Attesting Officer     Acting Commissioner of Patents and Trademarks